United States Patent
Wenger

(10) Patent No.: US 8,382,694 B2
(45) Date of Patent: Feb. 26, 2013

(54) ANKLE-FOOT ORTHOTIC FOR TREATMENT OF FOOT DROP

(75) Inventor: Jerry Wenger, Powell, WY (US)

(73) Assignee: JE3.LLC, St. Paul, MN (US)

( * ) Notice: Subject to any disclaimer, the term of this patent is extended or adjusted under 35 U.S.C. 154(b) by 267 days.

(21) Appl. No.: 12/892,664

(22) Filed: Sep. 28, 2010

(65) Prior Publication Data

US 2011/0082404 A1  Apr. 7, 2011

Related U.S. Application Data

(60) Provisional application No. 61/246,780, filed on Sep. 29, 2009.

(51) Int. Cl.
*A61F 5/00* (2006.01)

(52) U.S. Cl. ............... 602/23; 602/27; 602/28

(58) Field of Classification Search ............. 602/23–30, 602/60–62; 128/882; 2/44, 467; 482/79, 482/122, 124
See application file for complete search history.

(56) References Cited

U.S. PATENT DOCUMENTS

| | | | |
|---|---|---|---|
| 2,584,010 A * | 1/1952 | Goffredo | 602/28 |
| 3,527,209 A * | 9/1970 | Baker | 602/28 |
| 3,834,377 A | 9/1974 | Lebold | |
| 3,916,886 A | 11/1975 | Rogers | |
| 3,976,059 A | 8/1976 | Lonardo | |
| 4,554,912 A | 11/1985 | Haberman | |
| 4,817,589 A * | 4/1989 | Wertz | 602/28 |
| 5,020,523 A | 6/1991 | Bodine | |
| RE33,762 E | 12/1991 | Lonardo | |
| 5,219,324 A | 6/1993 | Hall | |
| 5,224,925 A | 7/1993 | Varn | |
| 5,259,834 A | 11/1993 | Wittmeyer | |
| 5,269,748 A | 12/1993 | Lonardo | |
| 5,277,699 A | 1/1994 | Williamson | |
| 5,298,013 A | 3/1994 | Lonardo | |
| 5,306,230 A | 4/1994 | Bodine | |
| 5,370,604 A | 12/1994 | Bernardoni | |
| 5,449,339 A | 9/1995 | Drennan | |
| 5,603,692 A | 2/1997 | Maxwell | |
| 5,700,237 A | 12/1997 | Hess | |
| 5,817,041 A | 10/1998 | Bader | |
| 5,860,423 A | 1/1999 | Thompson | |
| 6,102,881 A | 8/2000 | Quackenbush et al. | |
| 6,146,349 A | 11/2000 | Rothschild et al. | |

(Continued)

FOREIGN PATENT DOCUMENTS

| | | |
|---|---|---|
| EP | 1501456 | 2/2005 |
| EP | 1562526 | 8/2005 |

(Continued)

OTHER PUBLICATIONS

Sassi Pacer Drop Foot Support System, www.sassipacer.com, Dec. 22, 2009, 4 pages.

*Primary Examiner* — Michael A. Brown
(74) *Attorney, Agent, or Firm* — Patterson Thuente Christensen Pedersen, P.A.

(57) ABSTRACT

An ankle-foot orthotic is provided that treats steppage gate by preventing foot drop during movement. The orthotic having an ankle brace linked to a user's shoe by an elastic strap. The elastic strap having sufficient elasticity to provide the appropriate amount of tensile force to the shoe to prevent foot drop, while having sufficient flexibility to allow the user to naturally flex their foot and ankle during movement. The elastic strap comprises hook fasteners attachable to and removable from the shoe, such that the orthotic can be easily put on or taken off by the user.

26 Claims, 27 Drawing Sheets

U.S. PATENT DOCUMENTS

| | | |
|---|---|---|
| 6,695,797 B2 | 2/2004 | Trieloff |
| 6,926,687 B2 | 8/2005 | Shields |
| 6,945,947 B2 | 9/2005 | Ingimundarson et al. |
| D514,225 S | 1/2006 | Sassi |
| 7,077,818 B2 | 7/2006 | Ingimundarson et al. |
| 7,458,950 B1 | 12/2008 | Ivany |
| 7,666,158 B2 * | 2/2010 | Jacobsen et al. ............... 602/28 |
| 7,674,212 B2 | 3/2010 | Kruijsen et al. |
| 7,722,556 B2 | 5/2010 | Warner |
| 8,114,042 B2 * | 2/2012 | Klotz et al. ................ 602/28 |
| 2002/0129821 A1 | 9/2002 | Trieloff |
| 2004/0134500 A1 | 7/2004 | Ingimundarson et al. |
| 2005/0070833 A1 | 3/2005 | Shields |
| 2005/0126047 A1 | 6/2005 | Kruijsen |
| 2005/0234378 A1 | 10/2005 | Ingimundarson et al. |
| 2006/0270958 A1 | 11/2006 | George |
| 2007/0038169 A1 | 2/2007 | Alon et al. |
| 2007/0191193 A1 | 8/2007 | Backes et al. |
| 2008/0300525 A1 | 12/2008 | Shlomovitz |
| 2009/0105624 A1 | 4/2009 | Warner |
| 2010/0076361 A1 | 3/2010 | Kruijsen et al. |
| 2010/0087765 A1 | 4/2010 | Gainey |

FOREIGN PATENT DOCUMENTS

| | | |
|---|---|---|
| WO | WO 92/05751 | 4/1992 |
| WO | WO 93/17641 | 9/1993 |
| WO | WO 03/092560 A1 | 11/2003 |
| WO | WO 2004/043289 A2 | 5/2004 |
| WO | WO 2005/030088 A2 | 4/2005 |
| WO | WO 2005/034819 A1 | 4/2005 |
| WO | WO 2005/097014 A1 | 10/2005 |

* cited by examiner

ANKLE-FOOT ORTHOTIC FOR TREATMENT OF FOOT DROP

PRIORITY CLAIM

The present application claims priority to U.S. Provisional Application Ser. No. 61/246,780, filed Sep. 29, 2009, and entitled "ANKLE-FOOT ORTHOTIC FOR TREATMENT OF FOOT DROP", which is herein incorporated by reference in its entirety.

FIELD OF THE DISCLOSURE

The invention relates generally to treating steppage gait in persons suffering from a foot drop condition, and more specifically, to an apparatus and related methods for supporting the front portion of the foot to prevent foot drop and alleviate the steppage gait caused by the foot drop.

BACKGROUND OF THE DISCLOSURE

Foot drop, also commonly known as drop foot, is a common condition in which a person is unable to lift the front portion of one or both feet during walking or running due to a neurological or muscular condition which weakens the muscles of the foot. The condition causes the front portion of the person's foot to slap down on the floor or drag across the floor during walking or running. Persons suffering from foot drop often compensate by lifting the afflicted foot higher than normally necessary when moving to prevent the dropping foot from dragging or slapping on the floor. The irregular gait caused by the foot drop and the compensating movement by the person is known as a steppage gait.

Foot drop is typically treated by ankle-foot orthotics that either lock the person's ankle in place or support the front portion of the person's foot. However, the currently available ankle-foot orthotics often restrict the natural flexing motion of the ankle and foot during normal movement to prevent the foot drop motion, replacing the steppage gait with a different irregular gait. Ankle locking orthotics, such as the one described in U.S. Pat. No. 3,916,886, typically comprise rigid L-shaped members fitted against the back of the ankle and the underside of the foot to prevent the entire foot from flexing downwardly at the ankle. U.S. Pat. No. 3,916,886 is hereby incorporated by reference in its entirety. However, because the L-shape member completely prevents downward flexing of the ankle at the foot, the foot cannot make the slight downward flexing movement that naturally occurs during walking or running. Ankle-foot orthotics that provide support to the front portion of the foot also impede the natural flexing of the foot and ankle during a natural gait. These orthotics typically comprise straps anchored to the person's calf or ankle at one end and anchored to the person's foot or shoe at the other end as disclosed in U.S. Pat. Nos. 4,817,589 and 7,458,950, to provide a tensile force preventing downward motion of the foot. U.S. Pat. Nos. 4,817,589 and 7,458,950 are also hereby incorporated by reference in their entirety. However, the straps used are often static or only have a limited elasticity to ensure sufficient tensile force is applied to support the front portion of the foot. The inelasticity of the straps also prevents the natural flexing of the foot and ankle during normal movement. The limited flexibility of presently available ankle foot orthotics effectively replace the irregular steppage gait with an irregular gait In addition to being overly restrictive, currently available ankle-foot orthotics are often too bulky to fit easily into shoes. Similarly, currently available ankle-foot orthotics often require numerous straps or anchors to properly secure the orthotic to the person's ankle or foot increasing the difficulty of putting the orthotic on or taking it off. For example, the L-shaped members of ankle locking orthotics are often large and do not easily fit into shoes without extensive modification of the shoe. In addition, the rigidness of the L-shape member prevents wearers from pointing their toes to ease put on or takeoff the shoe. Similarly, strap orthotics often employ a plurality of straps and anchors that must be attached to the shoe or foot to properly attach the orthotic to the person's ankle and foot. The straps and the anchors may be difficult to remove from the shoe if the person wants to remove or change shoes. The complexity and the difficulty of putting on and taking off the currently available orthotics often cause wearers to spend considerable time putting on or taking off orthotic or forgoing the orthotic altogether.

An additional problem for strap orthotics is the positioning of the straps and where the straps are anchored on the wearer. Typically, the anchor locations for the straps are placed as high up on the calf as possible and as far down the foot or shoe as possible to achieve the maximum tensile force. However, the higher up the calf or further down the foot the anchor points are placed, the more visible and cumbersome the orthotic becomes for the user. Similarly, the greater the number of straps, the more support is provided for the foot. As with the positioning of the anchor locations, the greater the number of straps, the more visible and cumbersome the orthotic becomes for the wearer. Similarly, the positioning of the straps may be uncomfortable for users if the straps are pressed against the person's foot or ankle. The straps may rub against the person's legs or feet during movement causing chaffing or other discomfort.

SUMMARY OF THE DISCLOSURE

An embodiment of the present invention is directed to an ankle-foot orthotic for applying a pulling force to a wearer's shoe to counteract the effects of drop foot and prevent steppage gait. More specifically, the ankle-foot orthotic anchors the top of the wearer's shoe to an ankle brace around the wearer's ankle with an elastic strap. The elastic strap applies a tensile force to the top of the wearer's shoe to prevent steppage gait while still providing the necessary flexibility to allow the wearer to flex their foot and ankle naturally during walking or running. The ankle-foot orthotic also comprises a highly customizable engagement system for linking the orthotic to the wearer's shoe allowing the wearer to customize where the tensile force is directed and the amount of tensile force applied.

An ankle-foot orthotic for treating steppage gait according to an embodiment of the present invention generally comprises an ankle brace and an elastic strap. The ankle brace further comprises wings for wrapping around a wearer's ankle and also defines an exterior face and an interior face contacting the wearer's ankle. In an embodiment of the present invention, an ankle pad can be positioned between the wearer's ankle and interior face of the ankle brace to prevent discomfort to the wearer while wearing the ankle-foot orthotic. A primary strap loop for receiving the elastic strap is positioned on the exterior face of the ankle brace between the first and second wings. In operation, wrapping the ankle brace around the wearer's ankle positions the primary strap loop at the rear of the wearer's ankle.

The elastic strap defines a first end and a second end and is adapted to engage the wearer's shoe. The elastic strap can further comprise a hook fastener disposed at each end for engaging any looped structures on the wearer's shoes such as shoe laces or eyelets for receiving shoe laces. The hook fasteners allow for easy engagement of the shoe and customization as to the exact location that the tensile force provided by the elastic strap will be applied. Alternatively, the elastic strap can further comprise a strap adjustment mechanism having a first buckle and a second buckle positioned on the elastic strap. In this configuration, the first and second ends of the elastic strap are threaded through the looped structure on the shoe and looped back to the first and second buckle respectively. The strap adjustment mechanism allows the wearer to change the effective length of the elastic strap and correspondingly the tension applied by the elastic strap to the wearer's shoe.

According to an embodiment of the present invention, in operation, the elastic strap is threaded through the primary strap loop and wrapped around the wearer's ankle to engage the wearer's shoe. In this arrangement, the elastic strap is angled at an ideal angle and providing the correct tension force for maintaining the wearer's shoe in the correct position. Alternatively, the ankle brace can be wrapped around the wearer's ankle such that the primary strap loop is disposed at the front of the wearer's angle. In this configuration, the elastic strap is not wrapped around the wearer's ankle and instead directly engages the wearer's shoe.

According to an embodiment of the present invention, the ankle-foot orthotic can further comprise ring anchors engagable to any looped structure on the wearer's shoe, including the shoe lace eyelets. The ring anchors can be easily engaged by or disengaged from the hook fasteners of the elastic strap. Consequently, the ring anchors can significantly reduce the time necessary to put on and take off the ankle-foot orthotic as well as simply the customization of the ankle foot orthotic allowing wearers to quickly try out a plurality of positions and arrangements for engaging the wearer's shoe with the elastic strap.

According to an embodiment of the invention, the orthotic can further comprise a support fitted to the exterior of the ankle brace. The support is adapted to protect the rear of the user's ankle from chaffing or other discomfort from the elastic strap rubbing against the user's ankle during movement. The ankle support can comprise a rigid polymer to provide support for the user's ankle and preventing the user from feeling any discomfort from the shifting or stretching of the elastic strap while walking. The ankle support is countered to protect the user's ankle without inhibiting the user's flexibility so as to allow the user to walk without hindrance.

According to an embodiment of the present invention, the support can further comprise a strap adjustment assembly having an adjustable primary strap loop and two secondary strap loops positioned within cutouts in the support. The elastic strap can be threaded through the primary and secondary strap loops to form a u-shaped portion in the elastic strap. The length of the adjustable primary strap loop can be adjusted to increase or decrease the size of the u-shaped portion, which correspondingly changes the effective length of the elastic strap and the tension applied to the wearer's shoe. Alternatively, the strap adjustment assembly can comprise a fixed length primary strap loop and two secondary strap loops. In this configuration, the support comprises a plurality of cutouts for receiving the primary strap loop. Positioning the primary strap loop in the various cutouts changes the size of the u-shaped portion and correspondingly the tension applied to the wearer's shoe.

The above summary of the invention is not intended to describe each illustrated embodiment or every implementation of the present invention. The Figures and the Detailed Description that follow more particularly exemplify these embodiments.

BRIEF DESCRIPTION THE FIGURES

The invention may be more completely understood in consideration of the following detailed description of various embodiments of the invention in connection with the accompanying drawings, in which.

Figure 1:
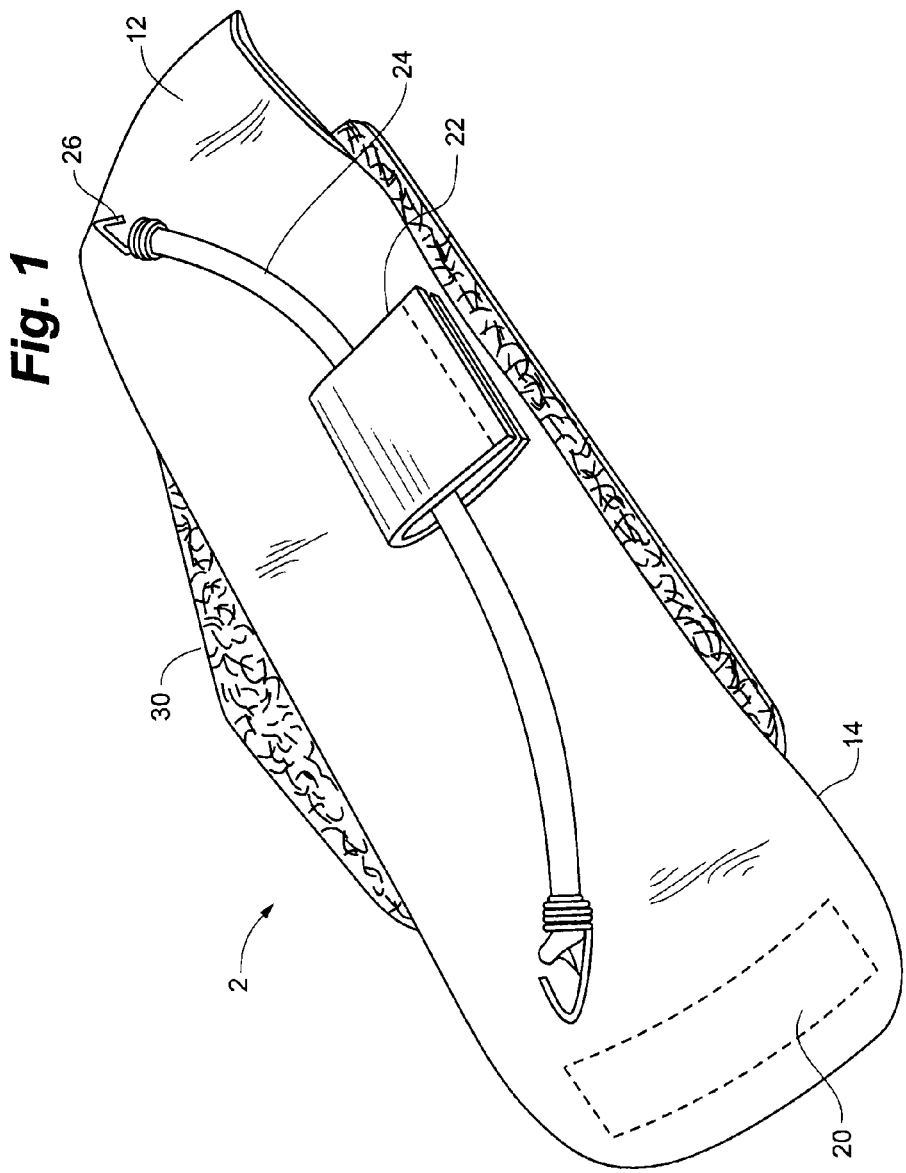
FIG. 1 is a perspective view of an ankle-foot orthotic in an unrolled configuration presenting the exterior face of the orthotic according to an embodiment.
Figure 2:
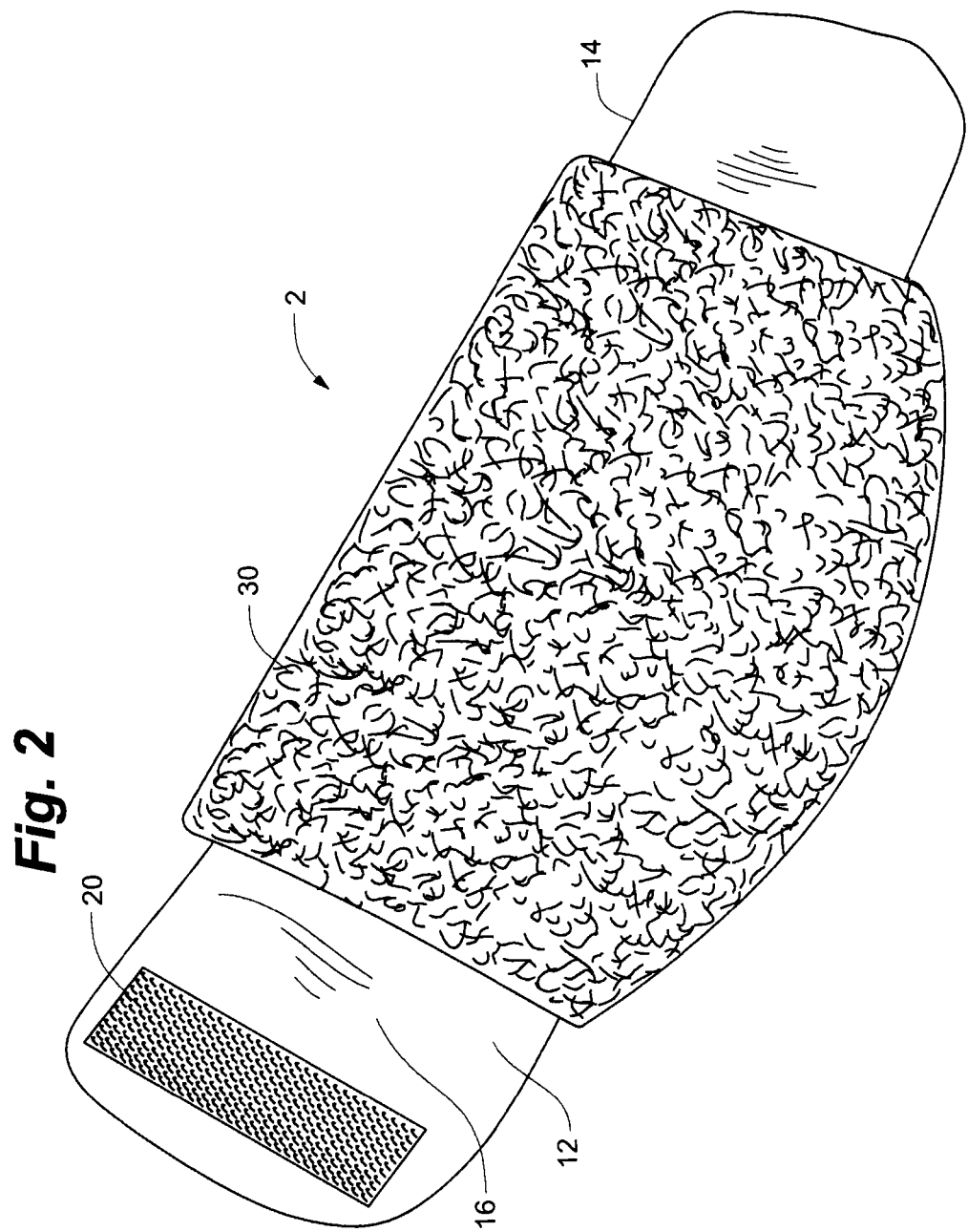
FIG. 2 is a perspective view of an ankle-foot orthotic in an unrolled configuration presenting the interior face of the orthotic according to an embodiment.
Figure 3:
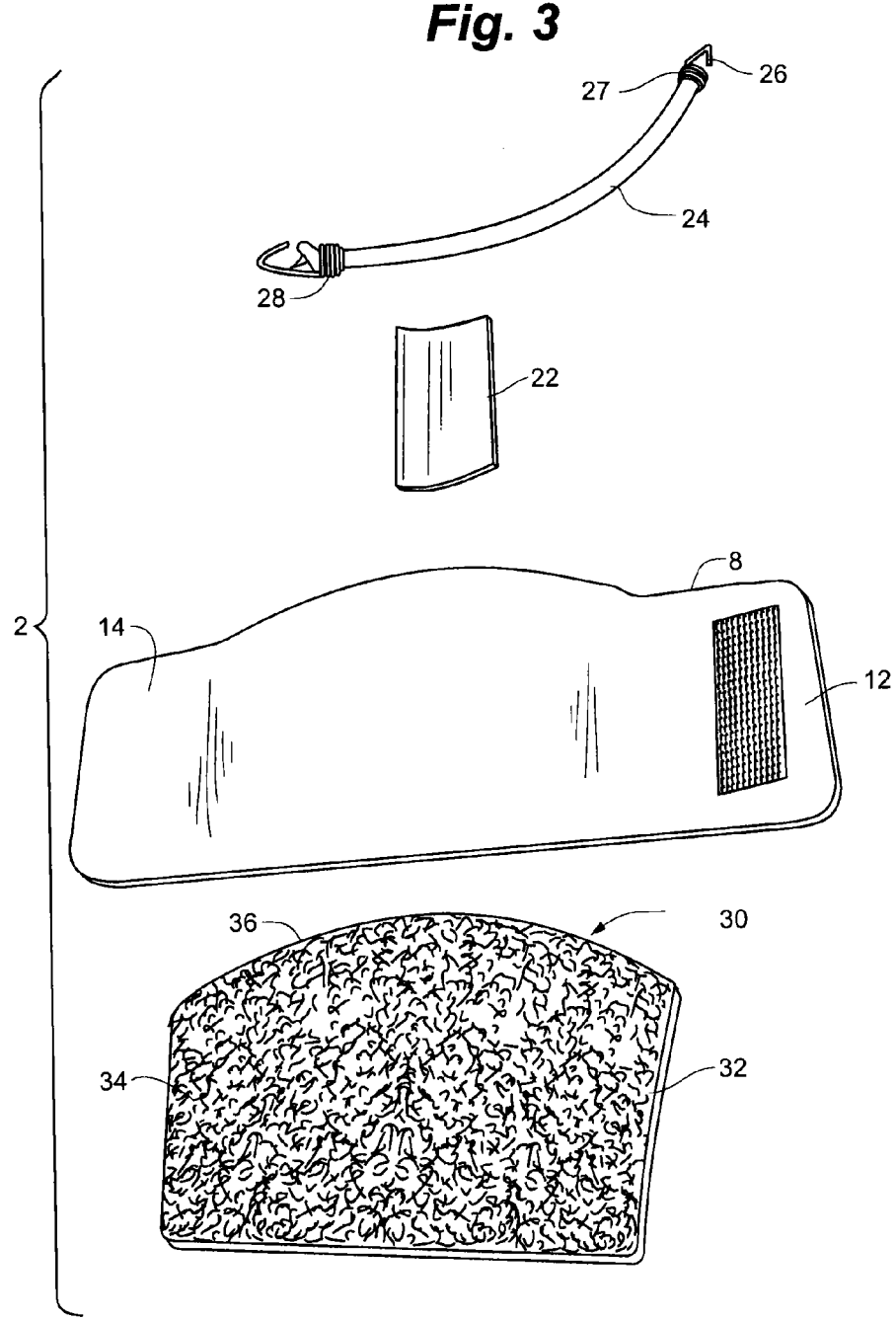
FIG. 3 is an exploded view of an ankle-foot orthotic according to an embodiment.
Figure 4:
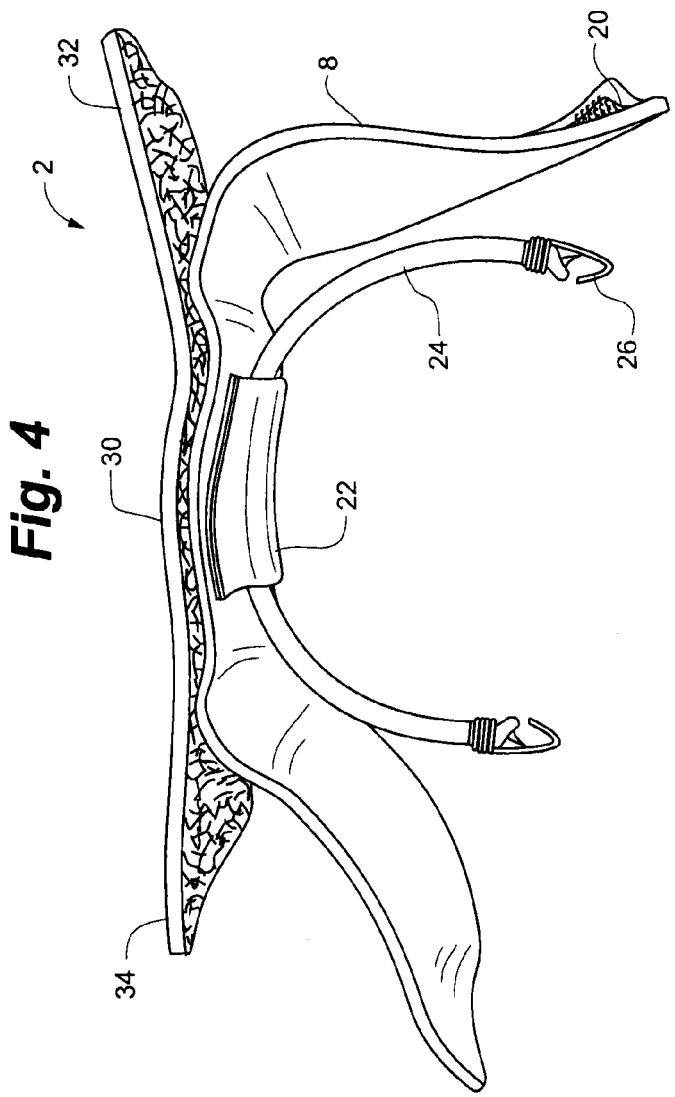
FIG. 4 is cross sectional view of an ankle-foot orthotic in an unrolled configuration according to an embodiment.
Figure 5:
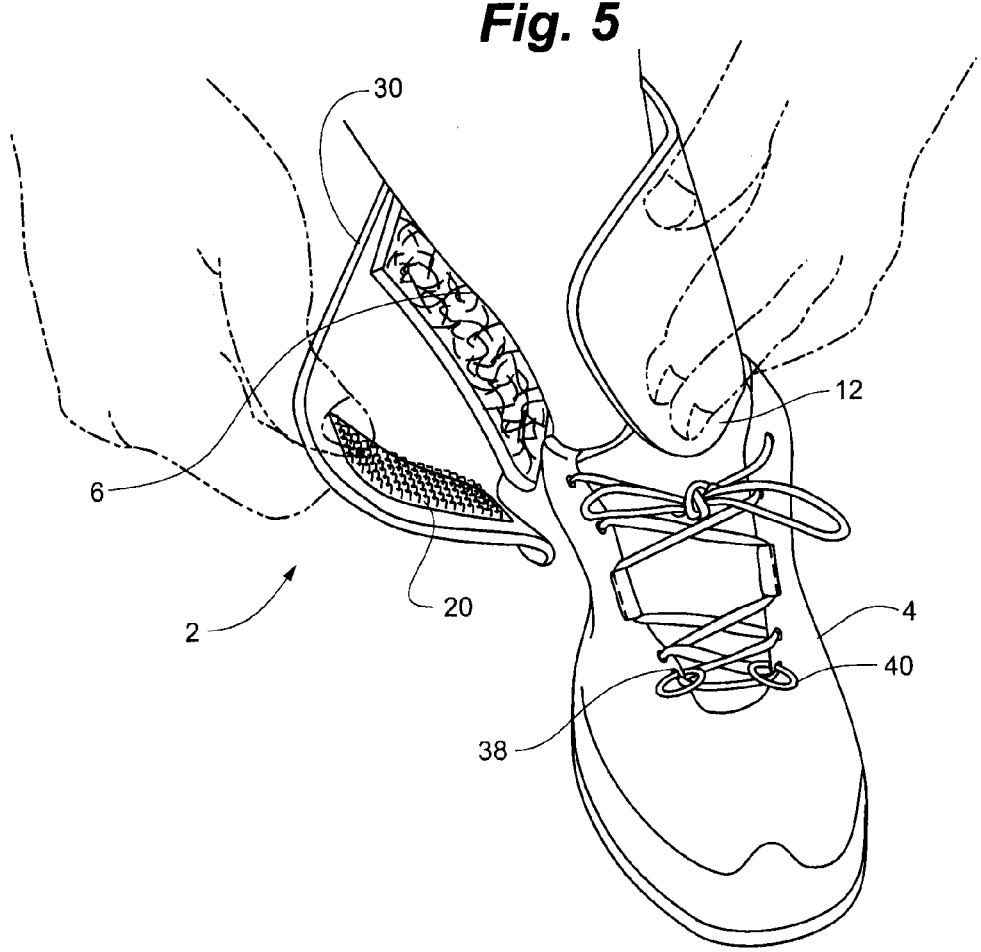
FIG. 5 is a front perspective view of an ankle-foot orthotic according to an embodiment wherein the ankle brace is being wrapped around a user's ankle.
Figure 6:
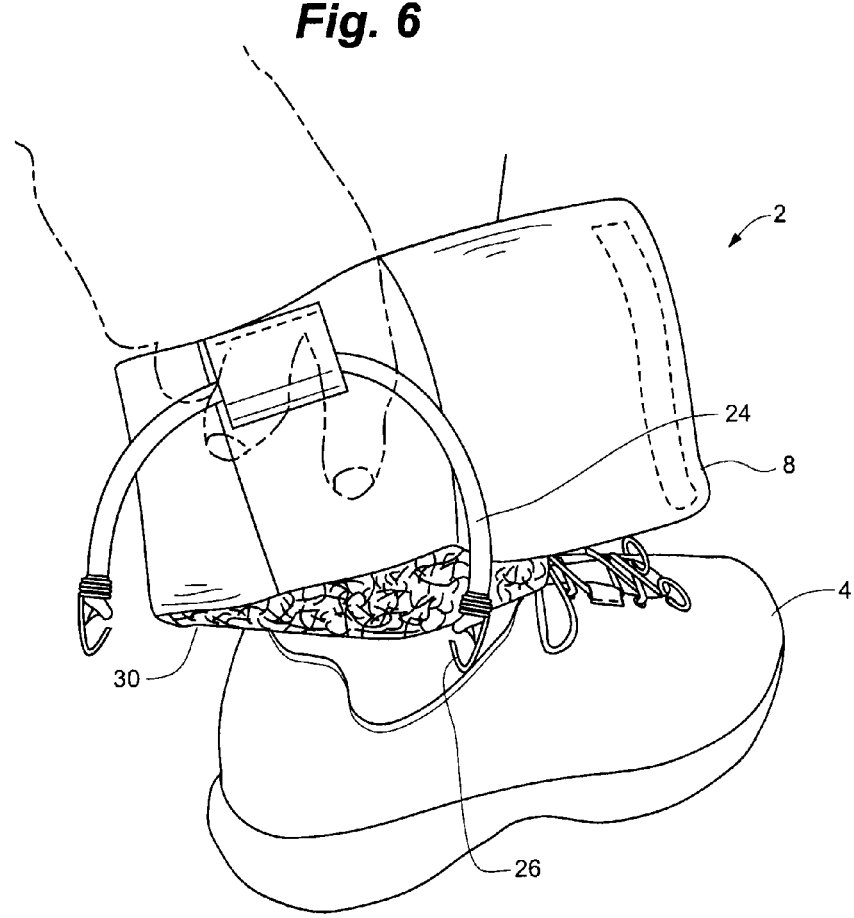
FIG. 6 is a rear perspective view of an ankle-foot orthotic according to an embodiment wherein the ankle brace is being wrapped around a user's ankle.
Figure 7:
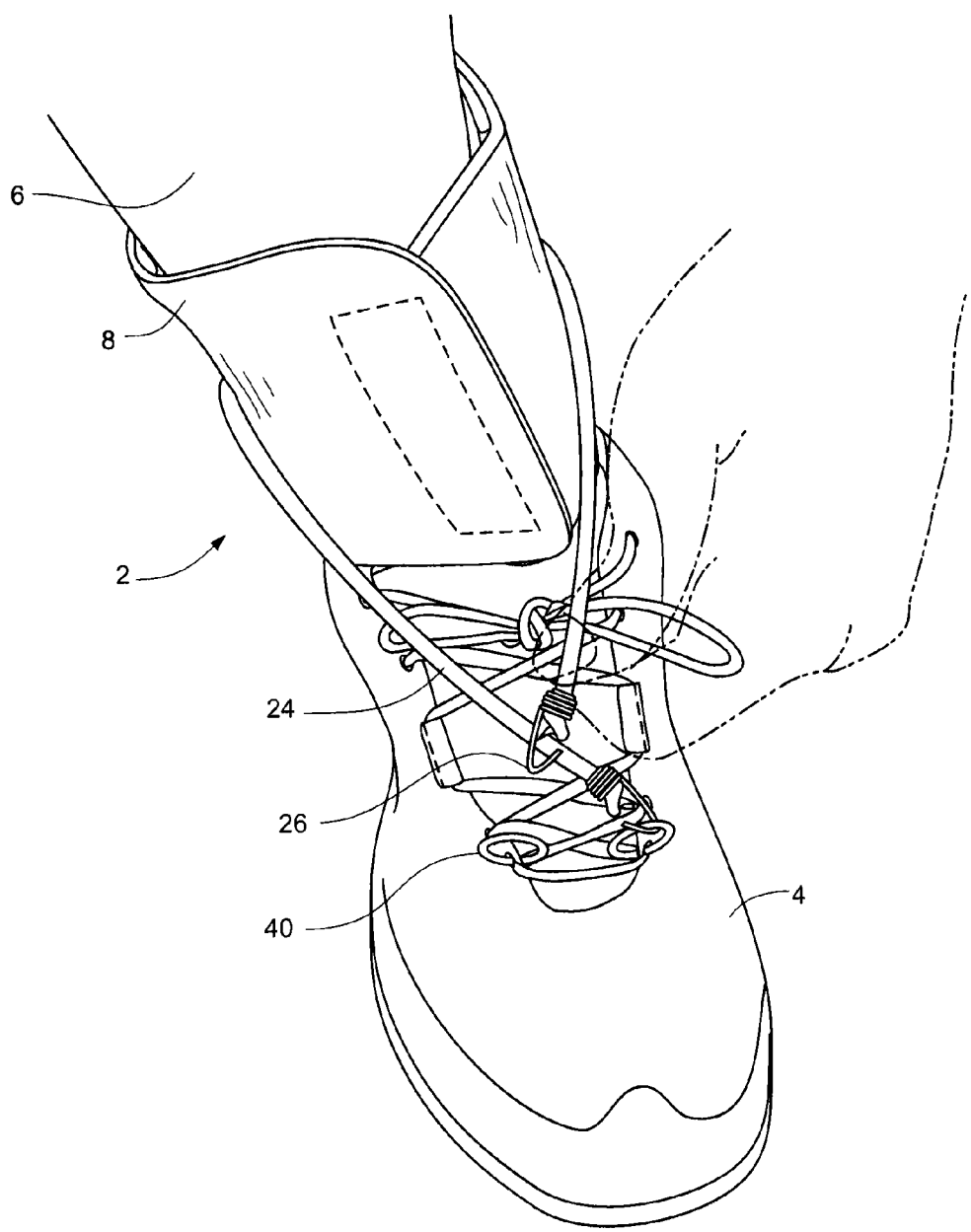
FIG. 7 is a perspective view of an ankle-foot orthotic according to an embodiment wherein the hook fasteners are being attached to the shoe.
Figure 8:
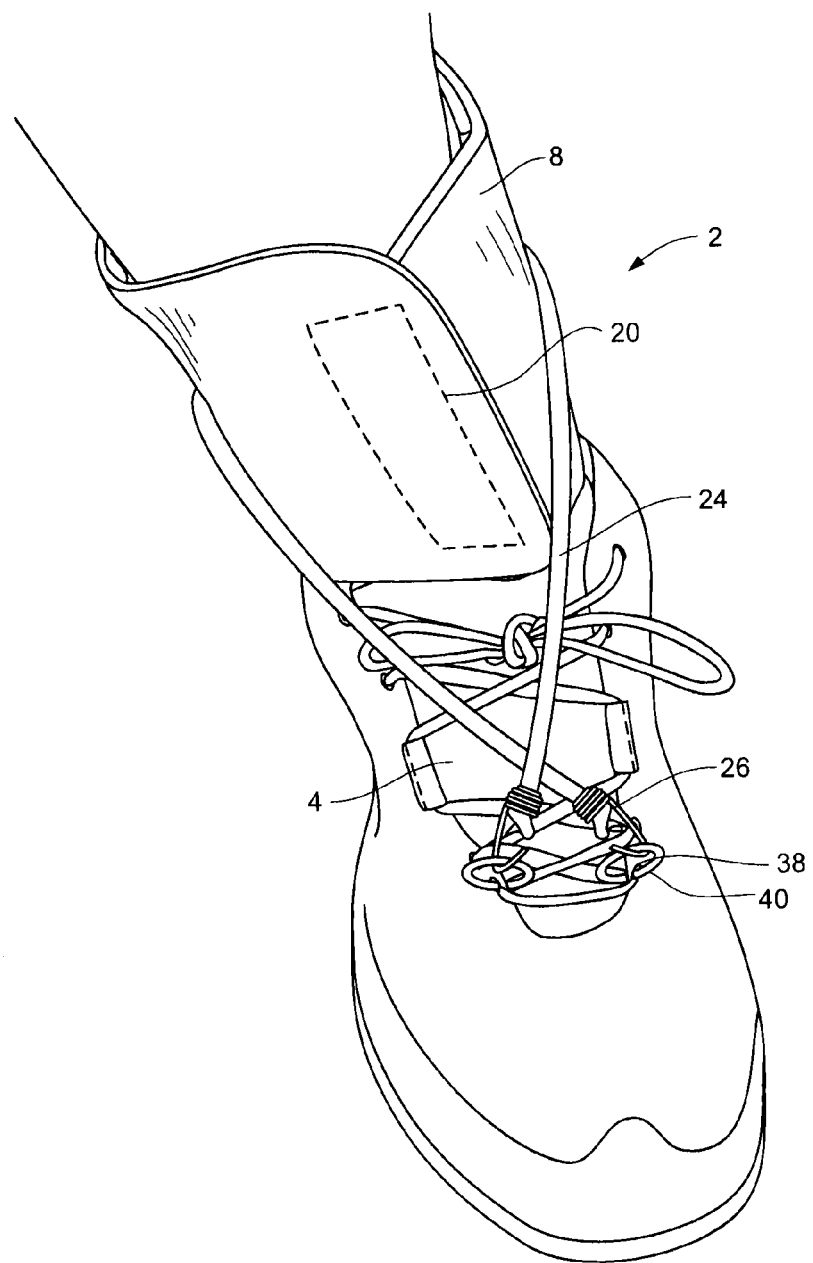
FIG. 8 is a front perspective view of a foot having an ankle-foot orthotic fully attached to the user's ankle and foot.
Figure 9:
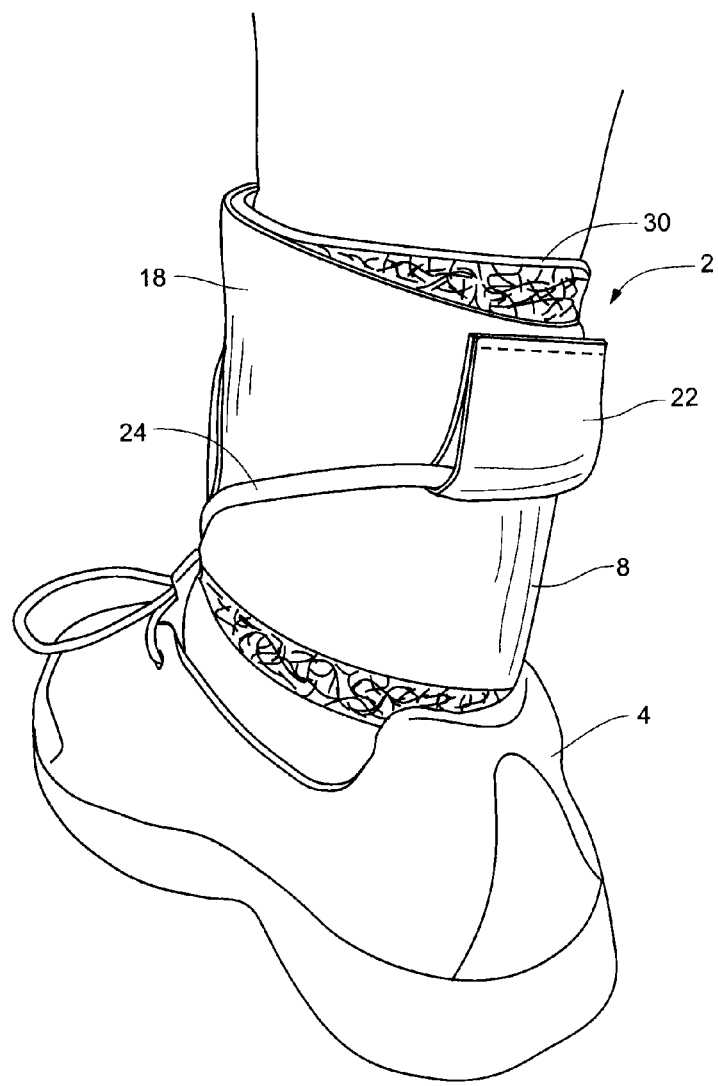
FIG. 9 is a rear perspective view of a foot having an ankle-foot orthotic fully attached to the user's ankle and foot.
Figure 10:
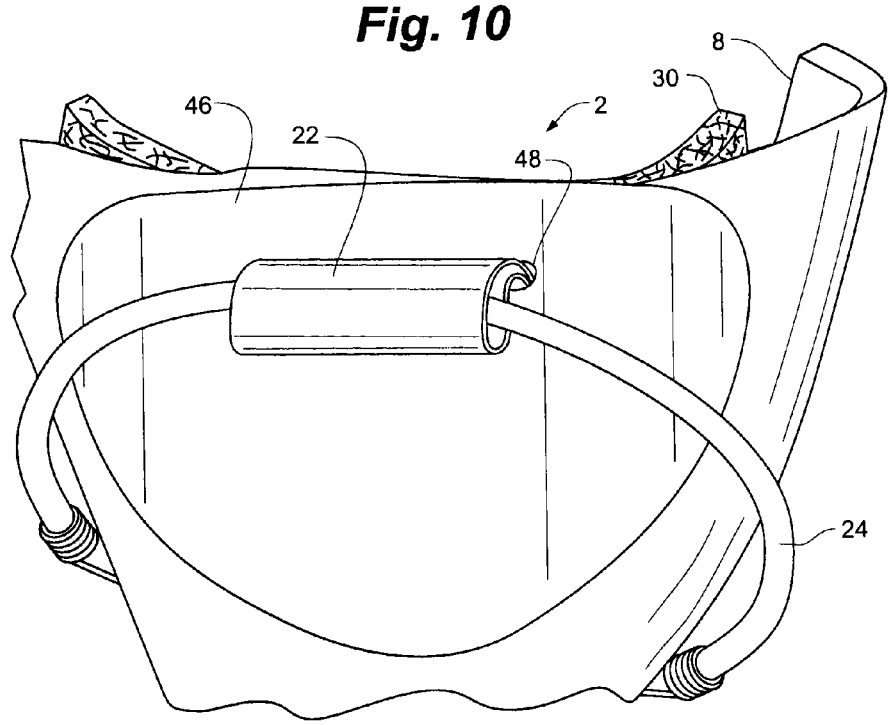
FIG. 10 is rear perspective view of an ankle-foot orthotic according to an embodiment of the invention.
Figure 11:
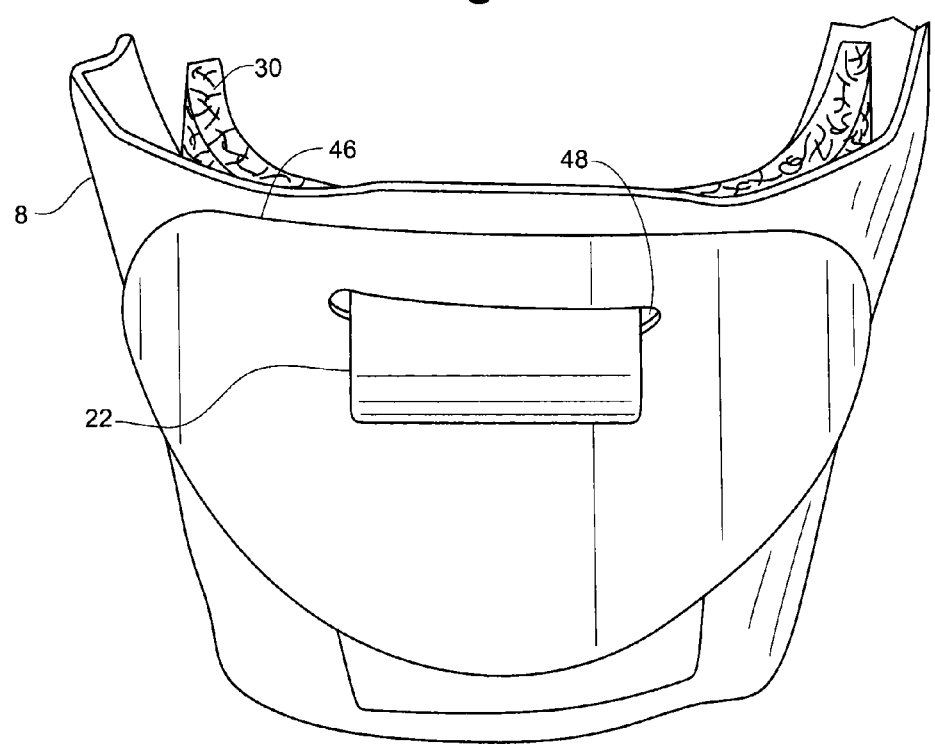
FIG. 11 is a rear perspective view of the ankle foot orthotic depicted in FIG. 10 with the elastic strap removed.
Figure 12:
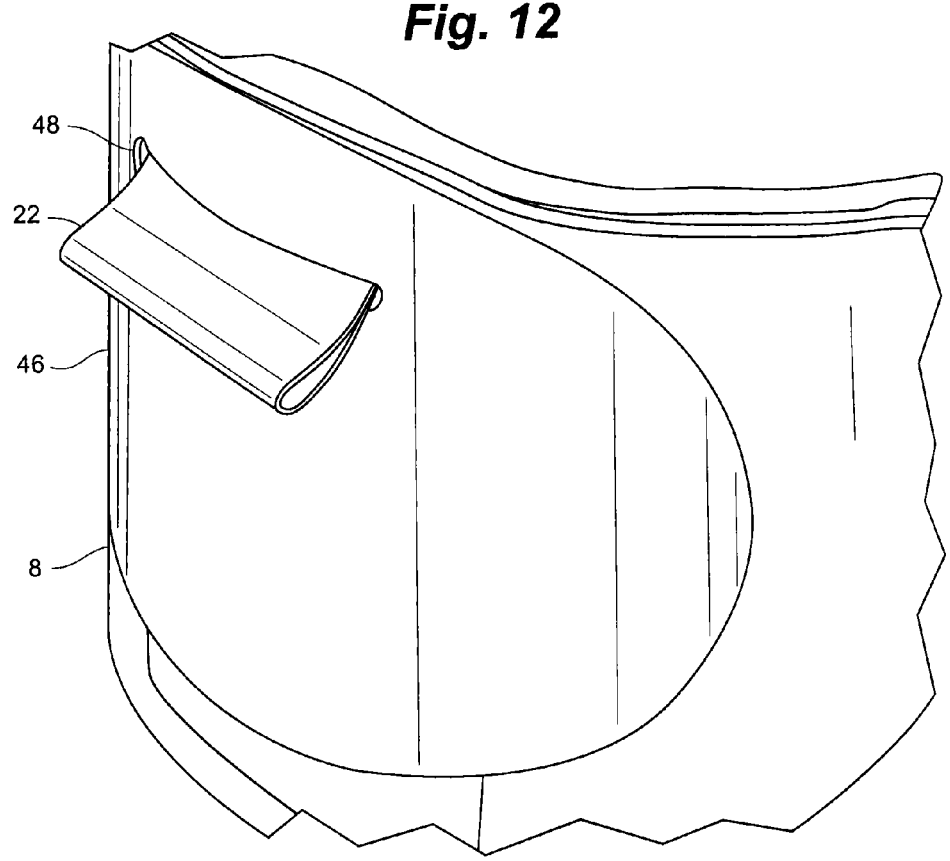
FIG. 12 is a side perspective view of the ankle foot orthotic depicted in FIG. 11.
Figure 13:
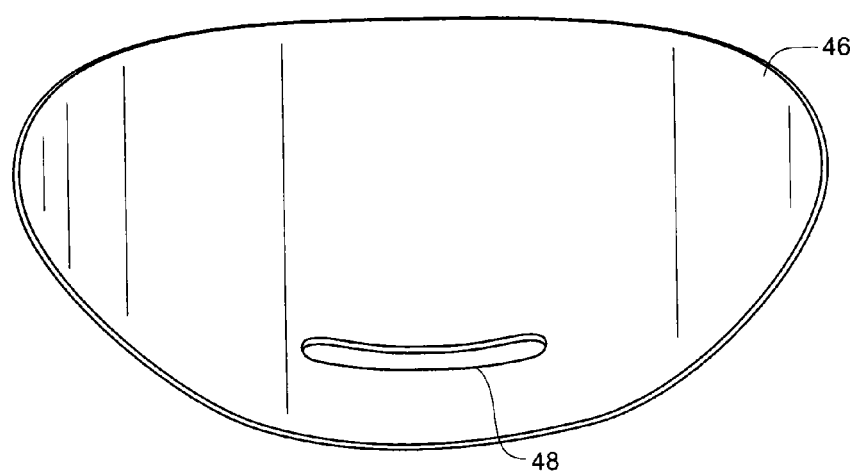
FIG. 13 is a perspective view of the interior side of a support for the ankle foot orthotic.
Figure 14:
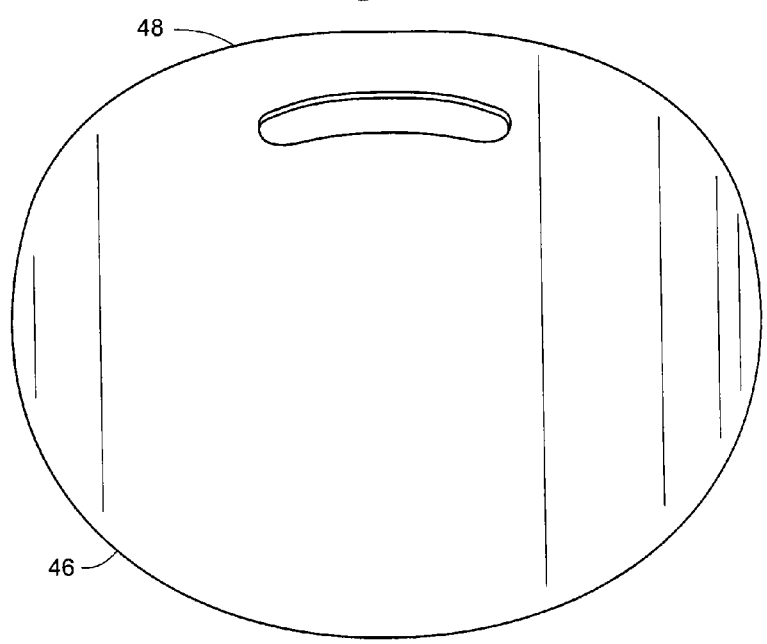
FIG. 14 is a perspective view of the exterior side of the support depicted in FIG. 13.
Figure 15:
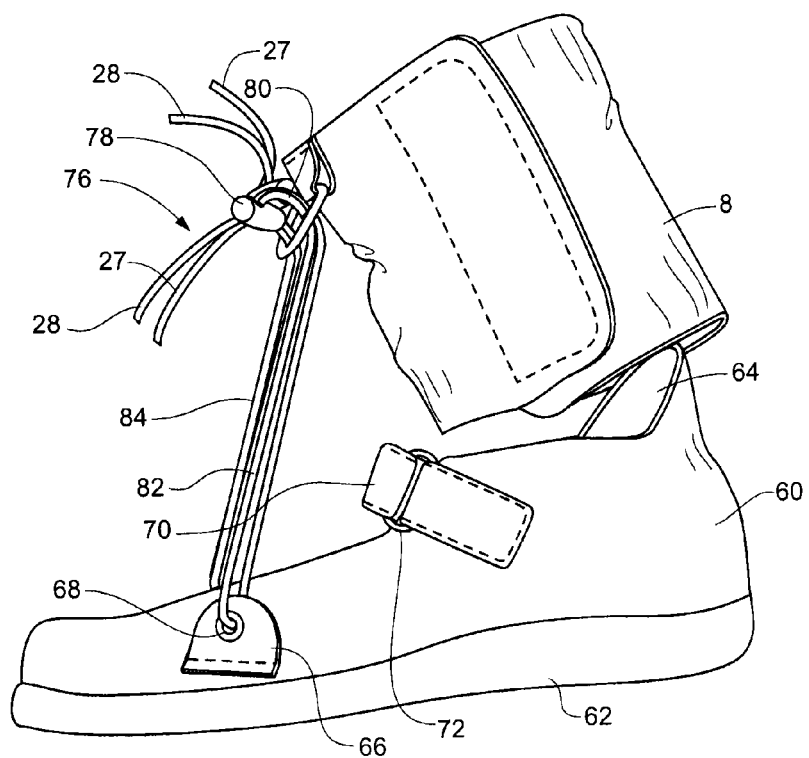
FIG. 15 is a side view of an ankle foot orthotic for a slipper according to an embodiment of the present invention.
Figure 16:
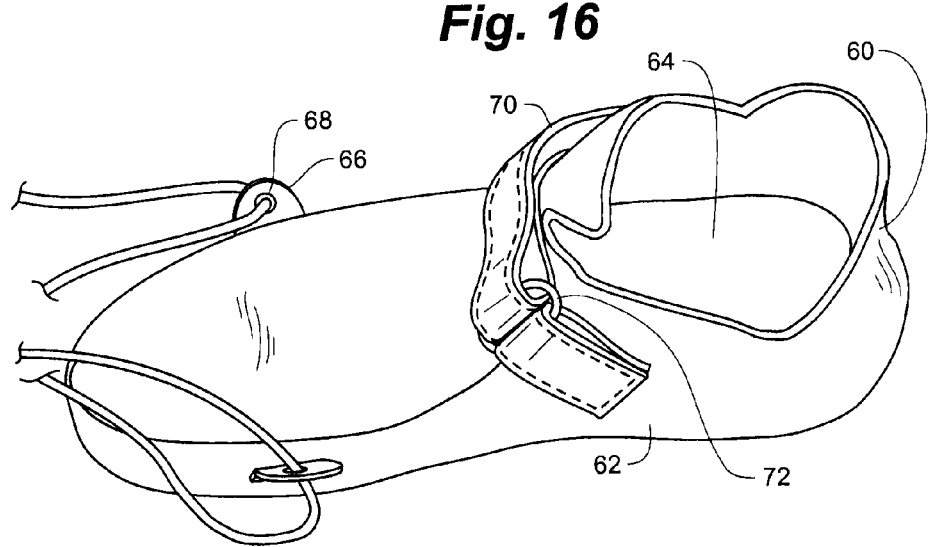
FIG. 16 is a top view of the slipper for the ankle foot orthotic depicted in FIG. 15.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE FIGURES

As illustrated in FIGS. 1-5, an ankle-foot orthotic 2 for treating steppage gait according to an embodiment of the present invention supports the weakened muscles by providing support beneath the wearer's foot or shoe 4 or by applying a pulling force to top of the wearer's shoe 4. The pulling force is typically provided by anchoring the front or top of wearer's foot or shoe 4 to the wearer's ankle 6.

Figure 17:
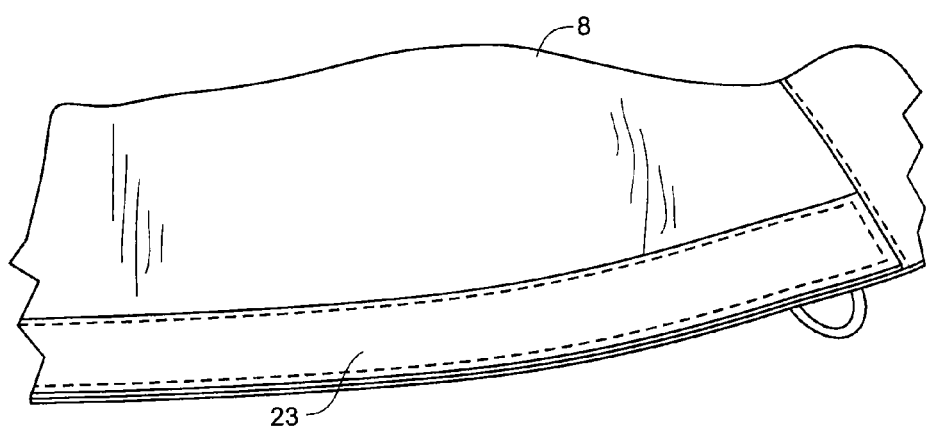
FIG. 17 is a side view of the ankle brace for the ankle foot orthotic depicted in FIG. 17 in the open configuration.
Figure 18:
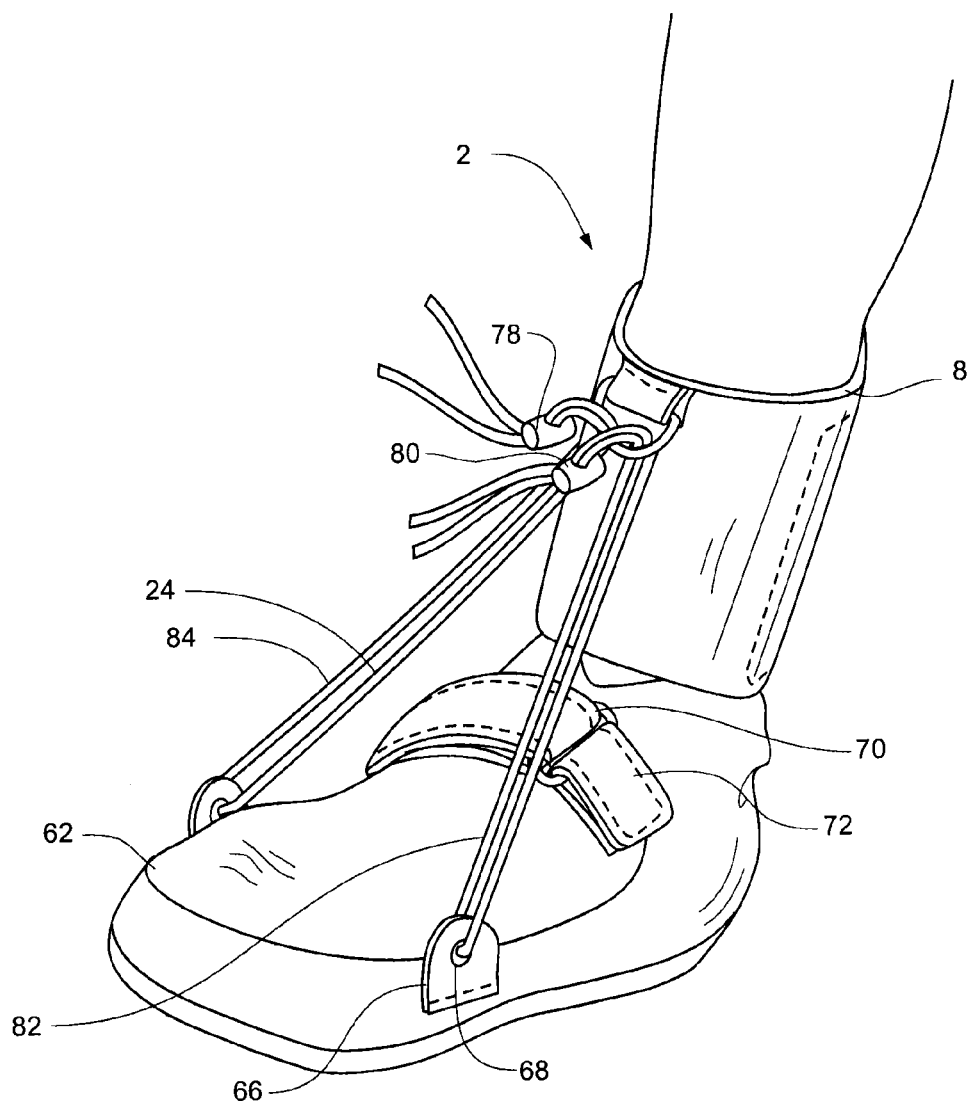
FIG. 18 is a perspective view of the ankle foot depicted in FIG. 15 fully attached to the user's ankle and foot.
Figure 19:
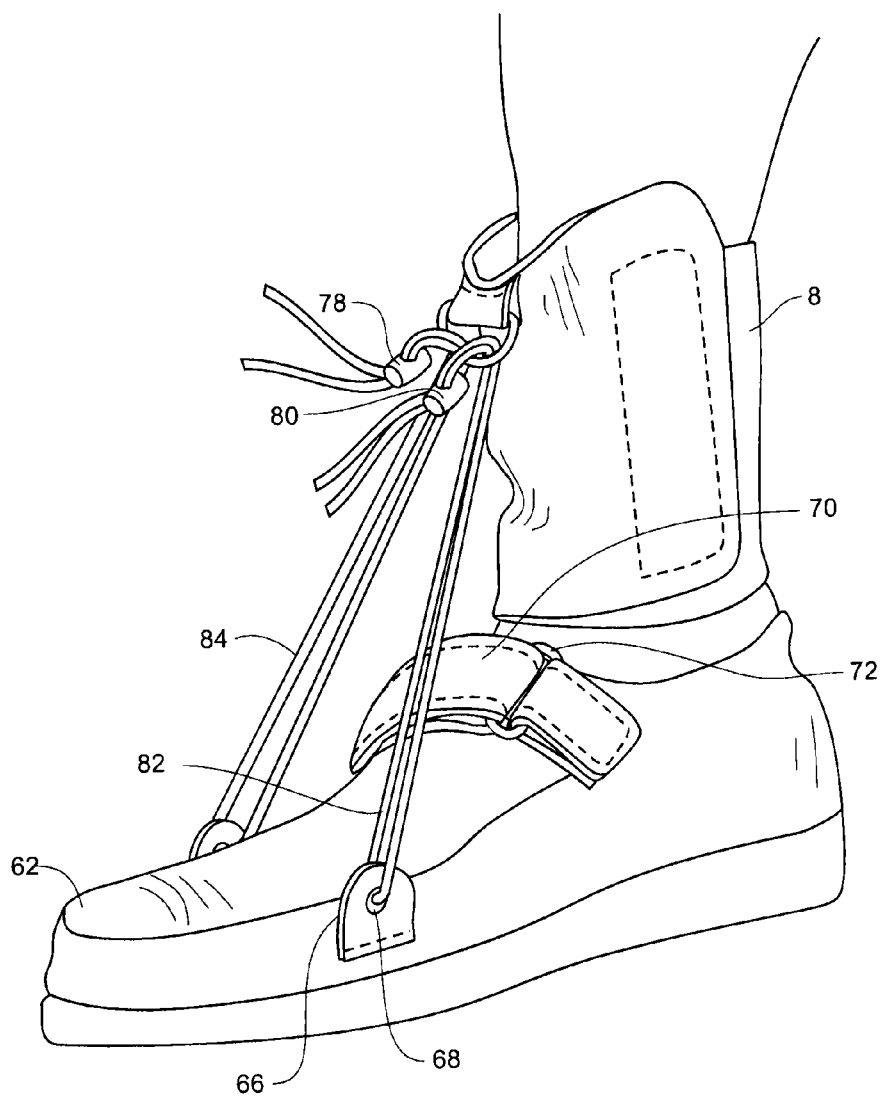
FIG. 19 is a perspective view of the ankle foot depicted in FIG. 15 fully attached to the user's ankle and foot.
Figure 20:
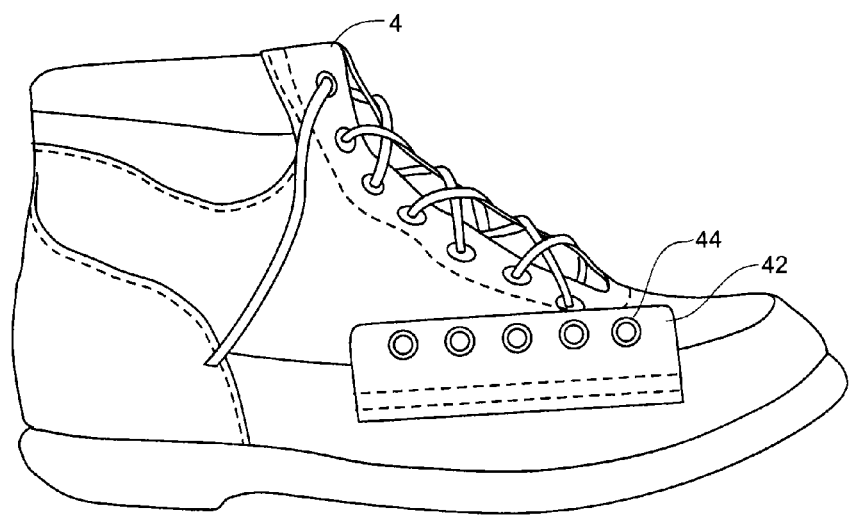
FIG. 20 is a side view of the grommet assembly according to an embodiment of the present invention.
Figure 21:
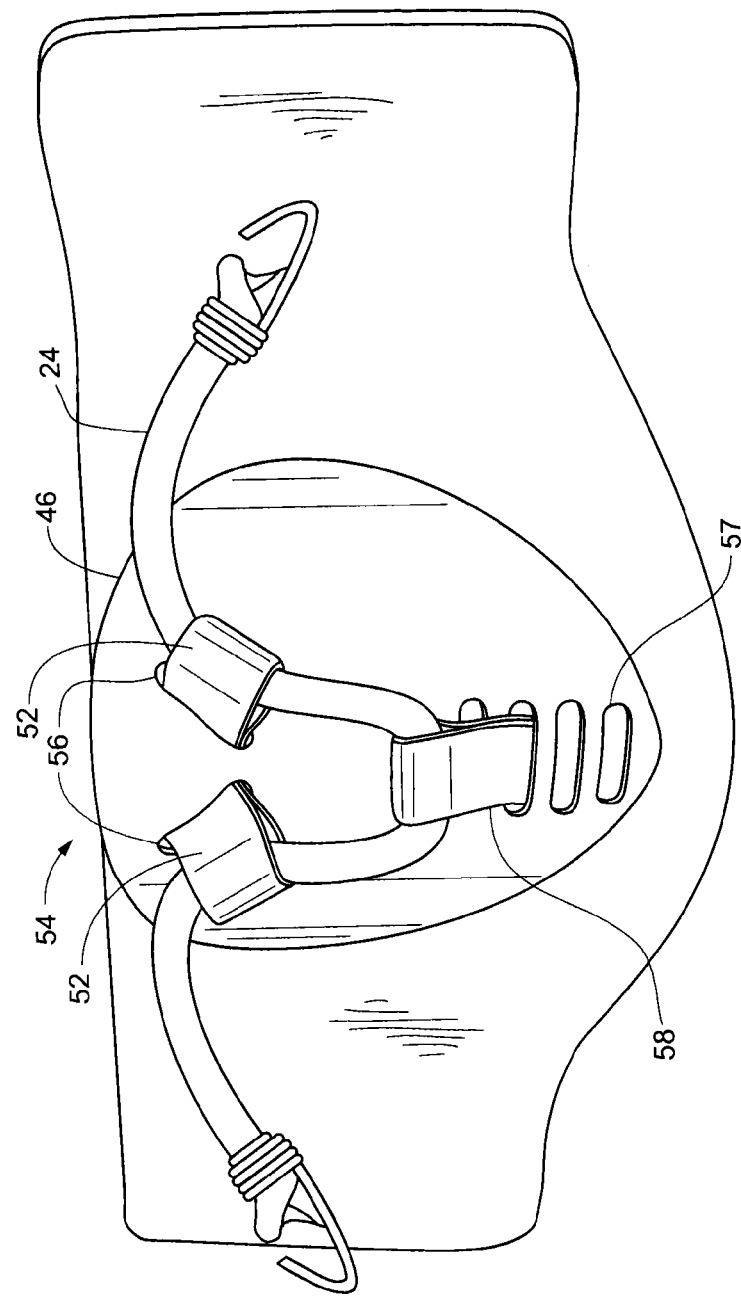
FIG. 21 is a rear perspective view of an elastic strap adjustment assembly according an embodiment of the present assembly.
Figure 22:
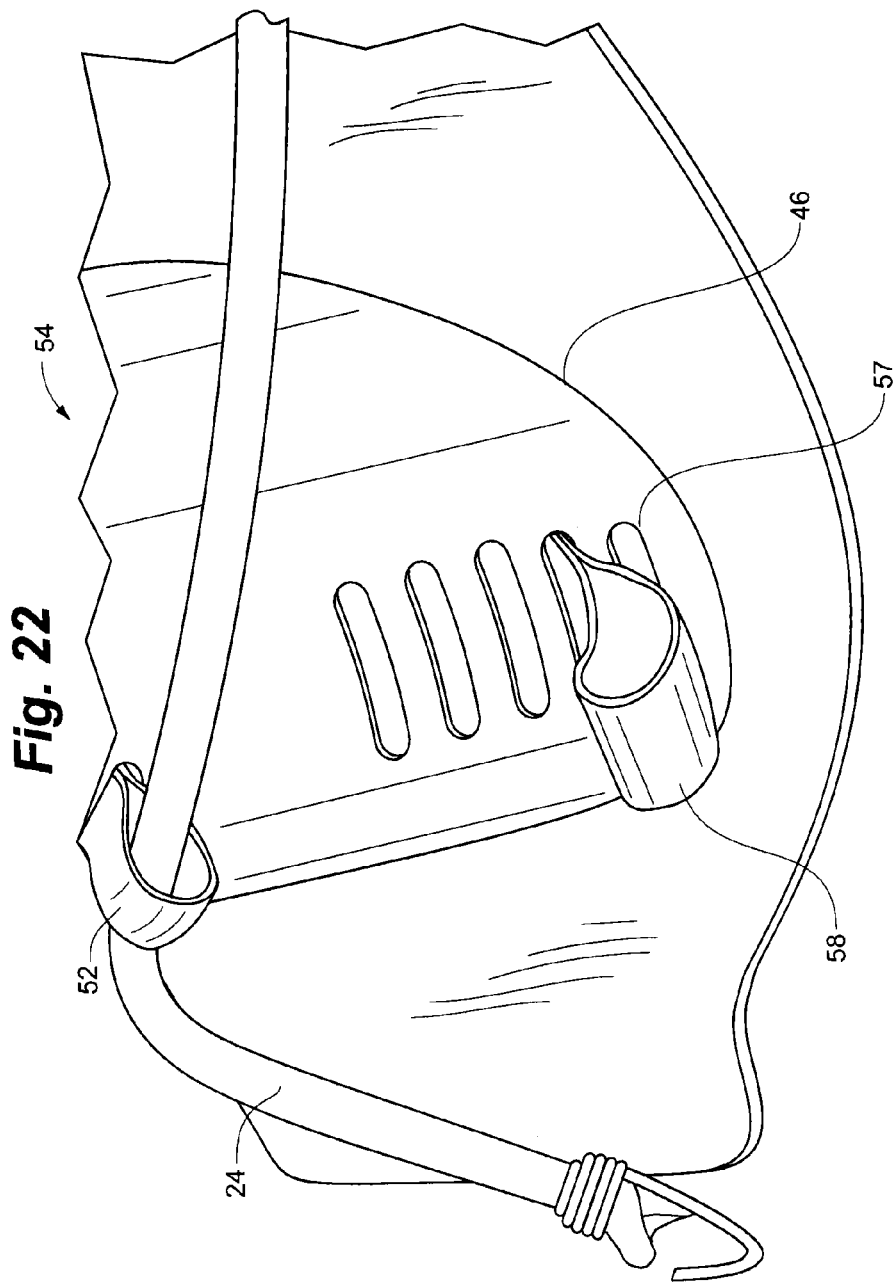
FIG. 22 is a rear perspective view of the elastic strap adjustment assembly depicted in FIG. 21.
Figure 23:
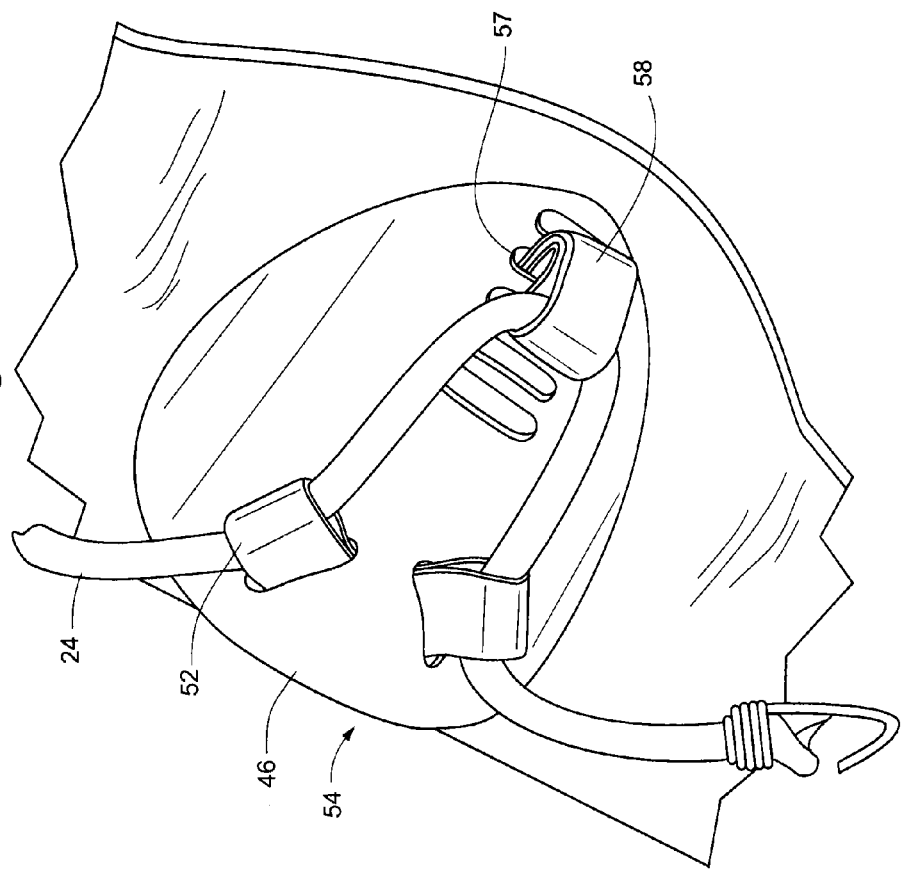
FIG. 23 is a rear perspective view of the elastic strap adjustment assembly depicted in FIG. 21.
Figure 24:
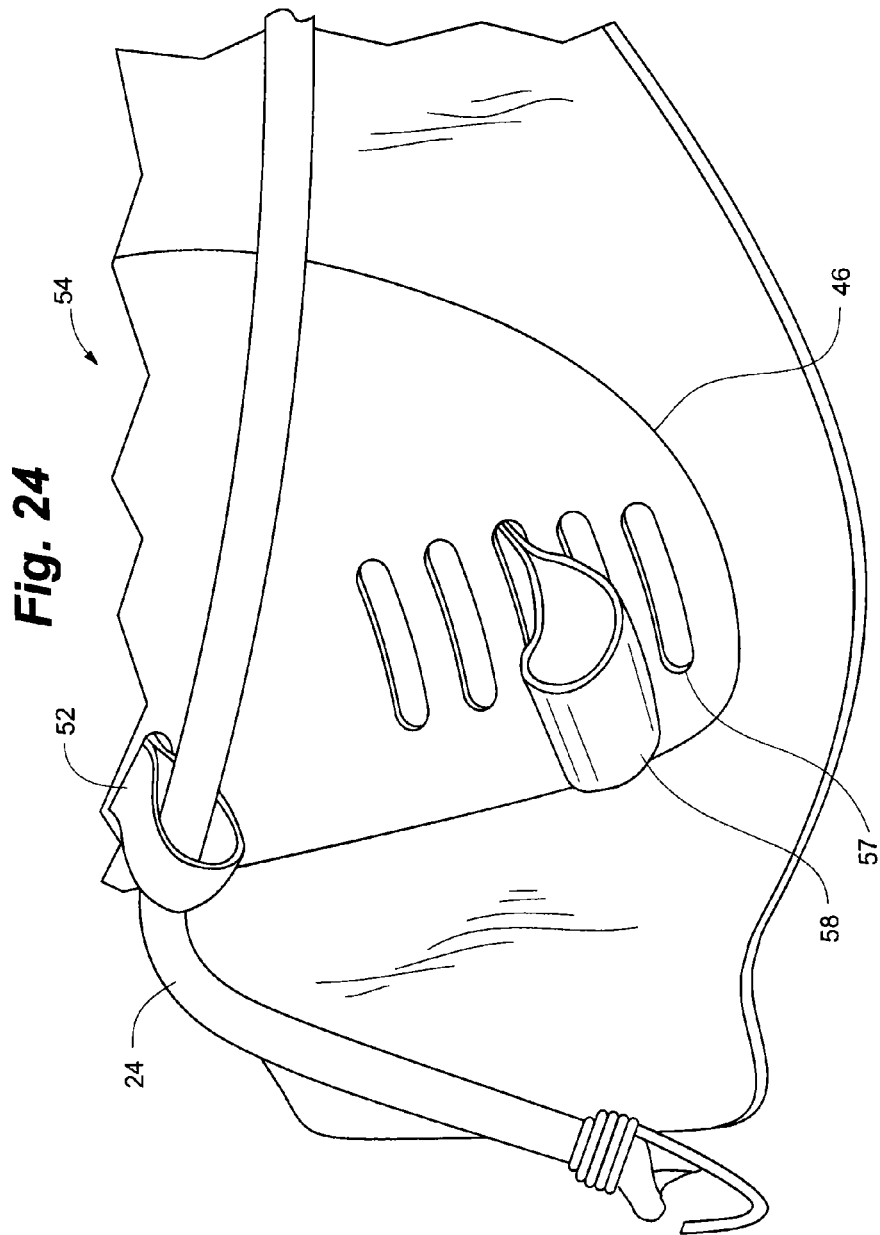
FIG. 24 is a rear perspective view of the elastic strap adjustment assembly depicted in FIG. 21.

The ankle-foot orthotic 2, according to an embodiment of the present invention, generally comprises an ankle brace 8 and an elastic strap 24. The ankle brace 8 further comprises a first wing 12 and a second wing 14 and defines an interior face 16 and an exterior face 18. The ankle brace 8 further comprises an ankle brace fastener 20 for releasably engaging the first wing 12 to the second wing 14 such that the ankle brace 8 forms a generally cylindrical shape around a wearer's ankle 6. The ankle brace fastener 20 can comprise a VELCRO fastener, an elastic fastener, button fastener or any other temporary fastening means. Similarly, the ankle brace 8 can be elastic material adapted to pull against the wearer's ankle 6 to maintain the position of the ankle brace 8 on the wearer's ankle 6. A primary strap loop 22 is disposed on the exterior face 18 of the ankle brace 8 between the first and second wing 12, 14. According to an embodiment of the present invention, the ankle brace 8 can further comprise a structural strap 23, as shown in FIG. 17, for maintaining the shape of the ankle brace 8 during movement and when tension force is applied to the ankle brace 8. The structural strap 23 comprises a flexible plastic material sufficiently rigid to withstand the tension forces applied to the ankle brace 8, but also sufficiently flexible to wrap around the user's ankle 6.

The elastic strap 24 defines a first end 27 and second end 28. The elastic strap 24 is threadable through the primary strap loop 22 and comprises an elastic material for applying a pulling force to the wearer's shoe 4. According to an embodiment of the present invention, different elastic straps 24 can be interchanged according the particular pull force required to prevent steppage gait or provide the desired flexibility for the wearer. The elastic strap 24 is sufficiently elastic to provide sufficient tensile force to prevent the foot 6 from inadvertently dropping due to foot drop, but has sufficient flexibility to allow the wearer to flex their foot and ankle 6 as need. As such, a wearer can walk or run using the ankle-foot orthotic 2 with the natural flexing of the foot and ankle 6. The elastic strap 24 further comprises a hook fastener 26 disposed at both the first and second end 27, 28. The hook fasteners 26 are adapted to engage any looped structure on the wearer's shoes 4 to operably link the ankle brace 8 to the wearer's shoes 4. According to an embodiment of the present invention, the hook fasteners 26 are shaped such that the point of the hook is at least parallel to the shank of the hook or points away from the shank to facilitate easy attachment and removal of the hook from the looped structures on the top of the shoe 4.

As illustrated in FIGS. 5 to 9, in operation, the first and second wings 12, 14 of the ankle brace 8 are wrapped around the wearer's ankle 6 such that the primary strap loop 22 extends outwardly from the rear of the wearer's ankle 6. In this configuration, the elastic strap 24 is wrapped around the ankle brace 8 and the wearer's ankle 6 before engaging the wearer's shoes 4. Wrapping the elastic strap 24 around the wearer's ankle 6 insures the correct tension is applied along the elastic strap 24 and properly angles the elastic strap 24 to maintain the wearer's shoe 4 in the proper position. Alternatively, the wings 12, 14 of the ankle brace 8 can be wrapped around the wearer's ankle 6 such that the primary strap loop 22 is positioned at the front of the wearer's ankle 6.

According to an embodiment of the present invention, the ankle brace 8 can further comprise an ankle pad 30 for protecting the wearer's ankle 6 from discomfort. The ankle pad 30 is disposed on the interior face 16 of the ankle brace 8 such that the ankle pad 30 is positioned between the ankle brace 8 and the wearer's ankle 6. The ankle pad 30 can comprise a foam, a mesh or other cushioning material to alleviate wearer discomfort. According to an embodiment of the present invention, the ankle pad 30 can be positioned on the ankle brace 8 such that the ankle pad 30 is positioned against the rear of the wearer's ankle 6 when the ankle brace 8 is wrapped around the wearer's ankle 6. In this configuration, the ankle pad 30 prevents the elastic strap 24 from chaffing or causing other discomfort to the wearer's ankle 6 when the elastic strap 24 is wrapped around the wearer's ankle 6 to engage the wearer's shoe 4. Alternatively, the ankle pad 30 can further comprise a first wing 32 and a second wing 34 (FIG. 4) adapted to wrap around the wearer's ankle 6 to protect both the sides and rear of the wearer's ankle 6 from discomfort.

The ankle pad 30 can further comprise a shoe cushion 36 (FIG. 3) for preventing chaffing between the wearer's shoe 4 and the ankle pad 30. The shoe cushion 36 similarly supports the ankle pad 30 to prevent the ankle brace 8 from sliding down the wearer's ankle 6 during use.

Referring to FIGS. 7 to 9 and 20, the elastic strap 24 comprises hook fasteners 26 for engaging any looped structure on the wearer's shoe 4. Typical shoes 4 can comprise eyelets 38 for receiving shoes laces. The hook fasteners 26 can engage either the laces, eyelets 38 or any other looped structure commonly found on conventional shoes 4. According to an embodiment of the present invention, at least one ring anchor 40 that are easily engageable by the hook fasteners 26 can be threaded through at least one of the eyelets 38. Alternatively, at least one grommet assembly 42 comprising a plurality of grommets 44 releasably engagable by the hook fasteners 26 can be affixed to the shoe 4. The grommet assembly 42 can be sewn, riveted or adhered with adhesive to the user's shoe or other conventional means of affixing the grommet assembly 42. According to an embodiment of the present invention, the grommet assembly 42 can comprise a fabric or leather construction to flex with the user's shoe 4 during walking or running.

As shown in FIGS. 7 to 9 and 20, wearers can customize the arrangement of the elastic strap 24 to accurately direct the tension force applied by the elastic strap 24 and maximize the effectiveness of the ankle foot orthotic 2. Foot drop can affect the various foot muscles differently from wearer to wearer and even from foot to foot, which can cause each afflicted foot to fall uniquely. For example, an afflicted foot can fall downwardly, roll or some combination thereof. As depicted, ring anchors 40 are positioned in only two of the eyelets 38, but can be positioned in each of the eyelets 38. A wearer can mix and match which ring anchor 40 to engage with the hook fasteners 26. For example, a wearer can engage both hook fasteners 26 to the same ring anchor 40 to maximize the force applied to the same part of the shoe 4. Similarly, the hook fasteners 26 can be positioned such that the elastic strap 24 crosses over the top of the shoe 4 or is uncrossed to properly direct the tension force.

Alternatively, as shown in FIGS. 15 to 19, the ankle brace 8 can be engaged to a slipper 60 according to an embodiment of the present invention instead of a conventional shoe 4. The slipper 60 comprises a slipper body 62 defining an internal volume 64 for receiving the wearer's foot and at least two tabs 66. Each tab 66 comprises an integrated ring 68 releasably engagable by hook fasteners 26. The slipper 60 can further comprise an adjustable strap 70 for adjusting the fit of the slipper body 60. The adjustable strap 70 further comprises buckle 72 and a strap fastener 74. The adjustable strap 70 is threadable through the buckle 72 and removably adhered to itself with the strap fastener 74. The fit of the slipper 60 can be adjusted by adjusting the length of the adjustable strap 70 threaded through the buckle 72.

As shown in FIGS. 10-14, an embodiment of the ankle-foot orthotic 2 further comprises a support 46 affixable to the exterior face 18 of the ankle brace 8. The support 46 defines a cutout 48 for receiving the primary strap loop 22 such that the primary strap loop 22 protrudes through the support 46. The elastic strap 24 is insertable through the protruding primary strap loop 22 such that the elastic strap 24 is stretched around the exterior of the support 46 to provide an additional layer between the elastic strap 24 and wearer's ankle 6. The support 46 can comprise a rigid polymer material to provide additional protection and support for the user's ankle 6. According to an embodiment of the present invention, the support 46 is permanently affixed to the ankle brace 8. The support 46 can be retained against the ankle brace 8 by the elastic strap 24 or affixed to the ankle brace 8 by stitching or adhesives.

The support 46 can also comprise a contoured shape to fit the user's ankle 6 to provide additional support for the user during movement and to insure the ankle-foot orthotic 2 closely follows the user's ankle 6. Similarly, the lower portion of the support 46 can be shaped to prevent the support 46 from hindering the user's movement or flexibility.

Figure 25:
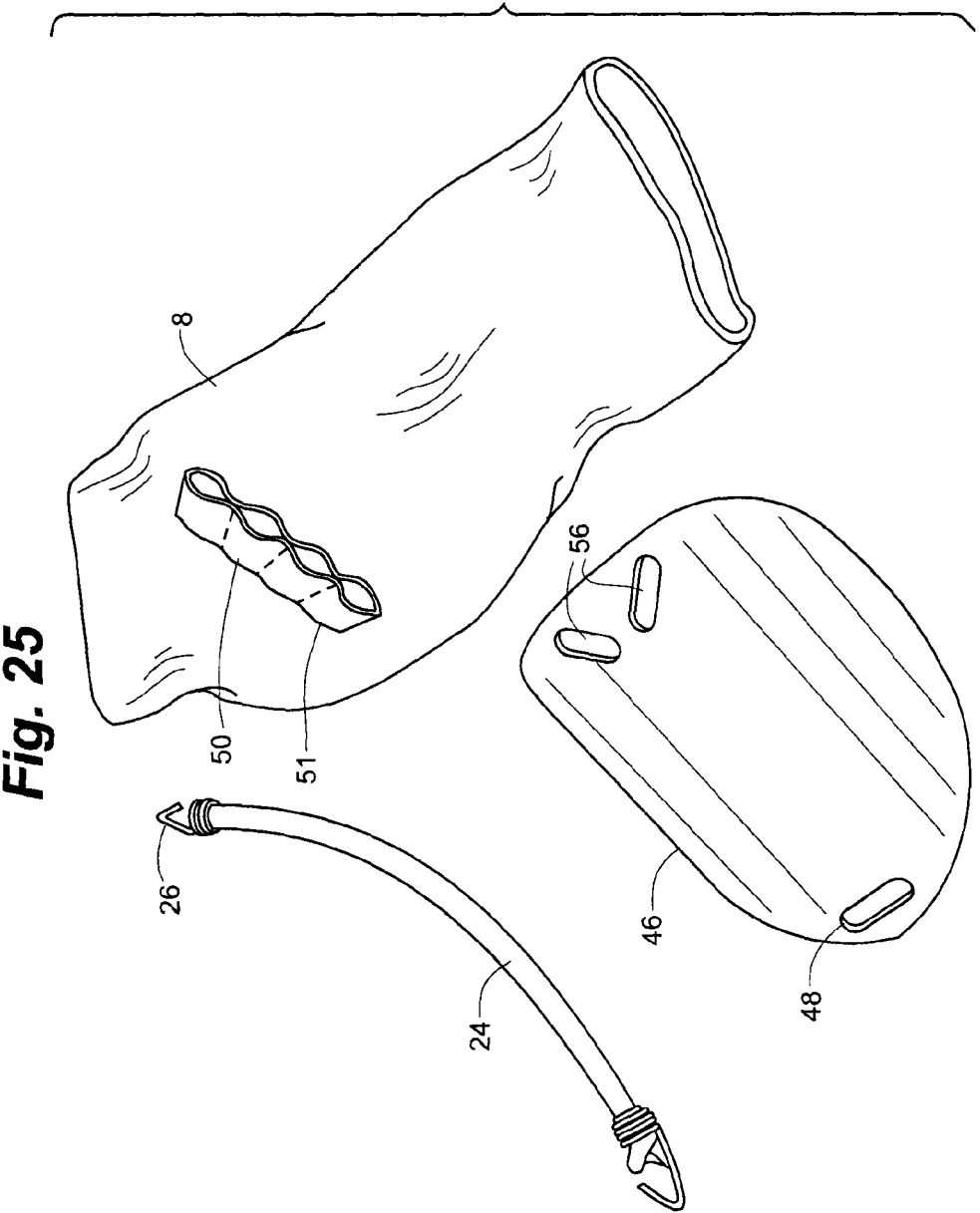
FIG. 25 is an exploded view of an ankle-foot orthotic having a tension adjustment assembly according to an embodiment.
Figure 26:
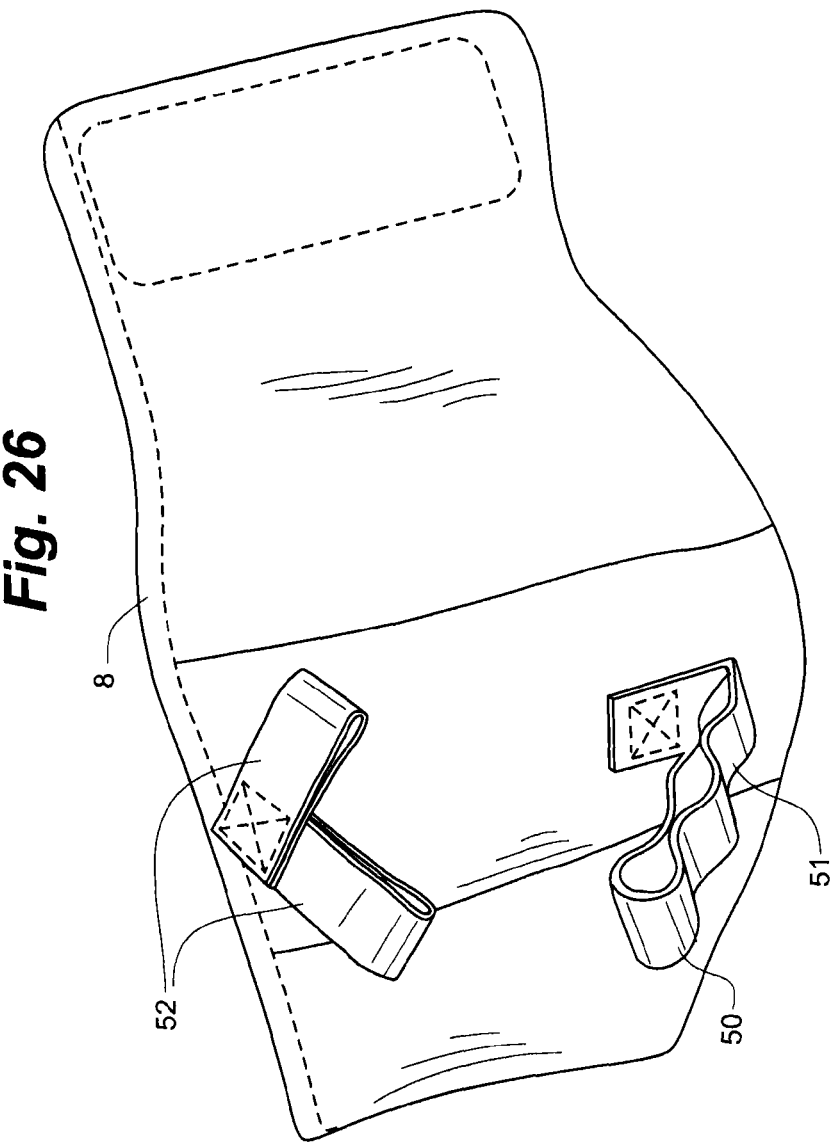
FIG. 26 is a perspective view of the ankle brace depicted in FIG. 25.
Figure 27:
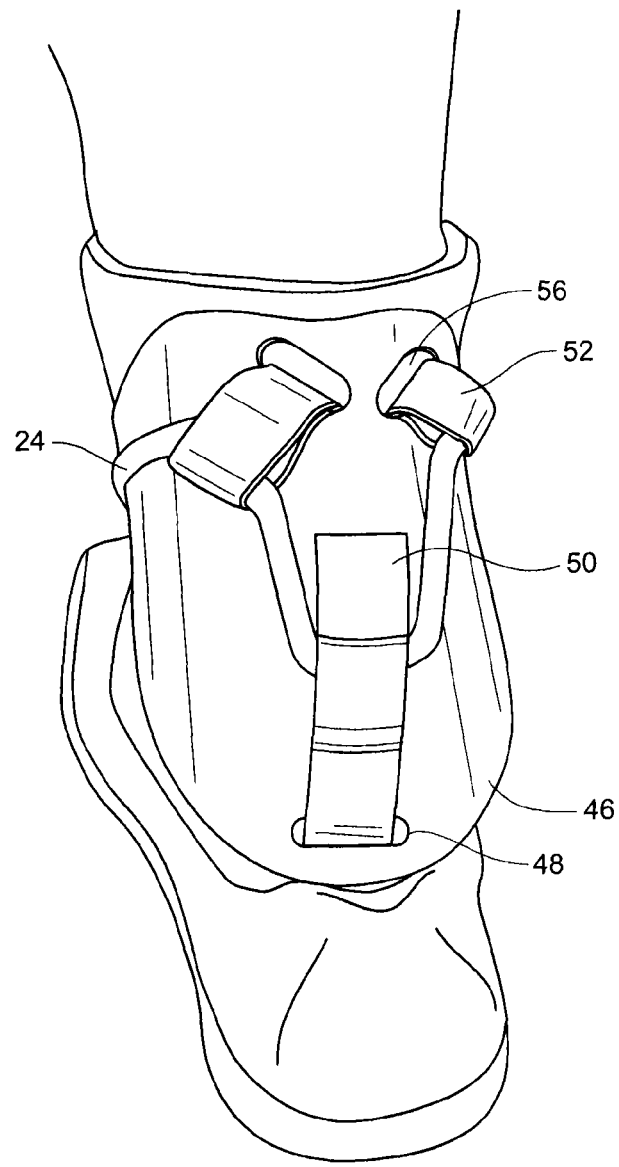
FIG. 27 is a rear perspective view of the ankle-foot orthotic depicted in FIG. 25.

As shown in FIGS. 21 to 27, the support 46 can further comprise a tension adjustment assembly 54 for adjusting the effective length of the elastic strap 24. The effective length of the elastic strap 24 is the portion of the elastic strap 24 extending from the rear of the wearer's ankle 6 to the wearer's shoe 4. The tension adjustment assembly 54 comprises a multi-loop primary strap loop 50 and two secondary strap loops 52 for receiving the elastic strap 24. As shown in FIGS. 25 to 27, primary strap loop 50 comprises a plurality of sub-loops 51. The primary strap loop 50 and the secondary strap loops 52 are affixed the exterior face 18 of the ankle brace 8. In this configuration, the support 46 comprises a primary cutout 48 for receiving the primary strap loop 50 and two secondary strap cutouts 56 for receiving the secondary strap loops 52.

In operation, the primary strap loop 50 and secondary strap loops 52 bend the elastic strap 24 into a u-shape within the tension adjustment assembly 54. Threading the elastic strap 24 through the various subloops 52 of the primary strap loop 50 changes the size of the u-shaped portion of the elastic strap 24 and changing the effective length of the elastic strap 24. Changing the effective length of the elastic strap 24 changes the tension force applied by the elastic strap 24.

As shown in FIGS. 21 to 24, the support 46 can alternatively comprise a plurality of primary cutouts 57 for receiving a fixed length primary strap loop 58. In this configuration, threading the primary strap loop 58 through the various primary cutouts 57 changes the size of the u-shaped portion and correspondingly the effective length of the elastic strap 24.

As shown in FIGS. 15 to 19, the elastic strap 24 can further comprise a strap adjustment assembly 76 comprising a first buckle 78 and a second buckle 80. In this configuration, the first and second ends 27, 28 are threaded through either the ring anchor 40 or the integrated ring 68 and folded back over the elastic strap 24 to form a first loop 82 and second loop 84. The first buckle 78 is positioned on the elastic strap 24 and adapted to receive the first end 27. The second buckle 80 is positioned on the elastic strap 24 and adapted to receive the second end 28. Sliding the buckles 78, 80 along the elastic strap 24 changes the effective length of the first and second loops 82, 84. Increasing the sizes of the loops 82, 84 reduces the effective length of the elastic strap 24 and increases the tension on the elastic strap 24, while reducing the sizes of the loops 82, 84 decreases the effective length of the elastic strap 24 and decreases the tension of the elastic strap 24.

Although specific examples have been illustrated and described herein, it will be appreciated by those of ordinary skill in the art that any arrangement calculated to achieve the same purpose could be substituted for the specific example shown. This application is intended to cover adaptations or variations of the present subject matter. Therefore, it is intended that the invention be defined by the attached claims and their legal equivalents.

What is claimed is:

1. An ankle-foot orthotic for treating foot drop comprising:
an ankle brace defining an exterior face and an interior face and having a first wing and a second wing positionable in an overlapping configuration and adapted for installation around a wearer's ankle such that the interior face faces inwardly toward wearer's ankle;
a primary strap loop positioned on the exterior face of the ankle brace so as to protrude outwardly from the rear of the ankle brace when the ankle brace is wrapped around the wearer's ankle; and
an elastic strap operably linking the ankle brace to a wearer's shoe for applying an upward resistive force to a wearer's shoe to prevent inadvertent downward movement of a wearer's foot, wherein the elastic strap is threadable through the strap loop such that the elastic strap wraps around the exterior face of the ankle brace and extends at a downward angle to engage the wearer's shoe.

2. The ankle-foot orthotic of claim 1, further comprising:
a rigid support affixed to the exterior face of the ankle brace and comprising a saddle-shape for contouring to the wearer's ankle.

3. The ankle-foot orthotic of claim 2, wherein the rigid support further comprises a cutout for receiving the primary strap loop, such that the elastic strap wraps around the rigid support when threaded through the elastic strap.

4. The ankle-foot orthotic of claim 1, further comprising:
an ankle pad positionable on the interior face of the ankle brace and the wearer's ankle.

5. The ankle-foot orthotic of claim 1, wherein the first wing comprises an adhering surface adapted to releasably adhere to the second wing.

6. The ankle-foot orthotic of claim 1, wherein the elastic strap defines a first end and a second, end each further comprising at least one hook fastener for releasably engaging any looped structures on the shoe.

7. The ankle-foot orthotic of claim 1, wherein the ankle brace further comprises:
- a first secondary strap loop for receiving the elastic strap; and
- a second secondary strap loop for receiving the elastic strap;
- wherein the primary strap loop further comprises a plurality of sub-loops for receiving the elastic strap;
- wherein a portion of the elastic strap is bendable into a u-shape by threading the elastic strap through one of the sub-loops of the primary strap loop and the secondary strap loops, wherein changing the size of the u-shaped portion changes the upward resistive applied by the elastic strap.

8. The ankle-foot orthotic of claim 7, wherein threading the elastic strap through different sub-loops of the primary strap loop changes the size of the u-shaped portion of the elastic strap.

9. An ankle foot orthotic system for treating foot drop comprising:
- a shoe defining a top surface and having a plurality of eyelets disposed on the top surface of the shoe for receiving a shoe lace;
- at least one ring fitted through at least one of the eyelets of the shoe;
- an ankle brace defining an exterior face and an interior face and having a first wing and a second wing positionable in an overlapping configuration and adapted for installation around a wearer's ankle such that the interior face faces inwardly toward wearer's ankle;
- a primary strap loop disposed on the exterior face of the ankle brace and adapted to protrude outwardly from the rear of the ankle brace when the ankle brace is wrapped around the wearer's ankle; and
- an elastic strap operably linking the ankle brace to a wearer's shoe for applying an upward resistive force to a wearer's shoe to prevent inadvertent downward movement of a wearer's foot, wherein the elastic strap is threadable through the strap loop such that the elastic strap wraps around the exterior face of the ankle brace and extends at a downward angle to engage the at least one ring.

10. The ankle-foot orthotic system of claim 9, further comprising:
- a rigid support affixed to the exterior face of the ankle brace and comprising a saddle-shape for contouring to the wearer's ankle.

11. The ankle-foot orthotic system of claim 10, wherein the rigid support further comprises a cutout for receiving the primary strap loop, such that the elastic strap wraps around the rigid support when threaded through the elastic strap.

12. The ankle-foot orthotic system of claim 9, further comprising:
- an ankle pad positionable on the interior face of the ankle brace and the wearer's ankle.

13. The ankle-foot orthotic system of claim 9, wherein the first wing comprises an adhering surface adapted to releasably adhere to the second wing.

14. The ankle-foot orthotic system of claim 9, wherein the elastic strap defines a first end and a second, end each further comprising at least one hook fastener for releasably engaging the at least one ring.

15. The ankle-foot orthotic system of claim 14, wherein the hook fasteners are adapted to releasably engage the at least one ring.

16. The ankle-foot orthotic system of claim 15, further comprises a grommet assembly having a plurality of grommets engagable by the hook fastener of the elastic strap.

17. The ankle-foot orthotic of claim 9, wherein the ankle brace further comprises:
- a first secondary strap loop for receiving the elastic strap; and
- a second secondary strap loop for receiving the elastic strap;
- wherein the primary strap loop further comprises a plurality of sub-loops for receiving the elastic strap;
- wherein a portion of the elastic strap is bendable into a u-shape by threading the elastic strap through one of the sub-loops of the primary strap loop and the secondary strap loops, wherein changing the size of the u-shaped portion changes the upward resistive applied by the elastic strap.

18. The ankle-foot orthotic of claim 17, wherein threading the elastic strap through different sub-loops of the primary strap loop changes the size of the u-shaped portion of the elastic strap.

19. An ankle foot orthotic system for treating foot drop comprising:
- a slipper defining a top surface and having at least one tab having at least one eyelet;
- an ankle brace defining an exterior face and an interior face and having a first wing and a second wing positionable in an overlapping configuration and adapted for installation around a wearer's ankle such that the interior face faces inwardly toward wearer's ankle;
- a primary strap loop disposed on the exterior face of the ankle brace and adapted to protrude outwardly from the rear of the ankle brace when the ankle brace is wrapped around the wearer's ankle; and
- an elastic strap operably linking the ankle brace to a wearer's shoe for applying an upward resistive force to a wearer's shoe to prevent inadvertent downward movement of a wearer's foot, wherein the elastic strap is threadable through the strap loop such that the elastic strap wraps around the exterior face of the ankle brace and extends at a downward angle to engage the at least one eyelet.

20. The ankle-foot orthotic system of claim 19, further comprising:
- a rigid support affixed to the exterior face of the ankle brace and comprising a saddle-shape for contouring to the wearer's ankle.

21. The ankle-foot orthotic system of claim 20, wherein the rigid support further comprises a cutout for receiving the primary strap loop, such that the elastic strap wraps around the rigid support when threaded through the elastic strap.

22. The ankle-foot orthotic system of claim 19, further comprising:
- an ankle pad positionable on the interior face of the ankle brace and the wearer's ankle.

23. The ankle-foot orthotic system of claim 19, wherein the first wing comprises an adhering surface adapted to releasably adhere to the second wing.

24. The ankle-foot orthotic system of claim 19, wherein the elastic strap defines a first end and a second, end each further comprising at least one hook fastener for releasably engaging the at least one eyelet of the slipper.

25. The ankle-foot orthotic of claim 19, wherein the ankle brace further comprises:

a first secondary strap loop for receiving the elastic strap; and a second secondary strap loop for receiving the elastic strap;

wherein the primary strap loop further comprises a plurality of sub-loops for receiving the elastic strap;

wherein a portion of the elastic strap is bendable into a u-shape by threading the elastic strap through one of the sub-loops of the primary strap loop and the secondary strap loops, wherein changing the size of the u-shaped portion changes the upward resistive applied by the elastic strap.

26. The ankle-foot orthotic of claim 25, wherein threading the elastic strap through different sub-loops of the primary strap loop changes the size of the u-shaped portion of the elastic strap.

* * * * *

UNITED STATES PATENT AND TRADEMARK OFFICE
CERTIFICATE OF CORRECTION

| | | |
|---|---|---|
| PATENT NO. | : 8,382,694 B2 | Page 1 of 1 |
| APPLICATION NO. | : 12/892664 | |
| DATED | : February 26, 2013 | |
| INVENTOR(S) | : Wenger | |

It is certified that error appears in the above-identified patent and that said Letters Patent is hereby corrected as shown below:

In the Specification

<u>Column 3, Line 22</u>:
After "wear's" delete "angle" and insert -- ankle --.

Signed and Sealed this
Eighteenth Day of March, 2014

Michelle K. Lee
*Deputy Director of the United States Patent and Trademark Office*